United States Patent
Hur et al.

(10) Patent No.: US 11,067,559 B2
(45) Date of Patent: Jul. 20, 2021

(54) OPTICAL SWITCH WITH REFLECTION DISK IN EXPLOSION-PROOF GAS DETECTOR

(71) Applicant: Honeywell International Inc., Morris Plains, NJ (US)

(72) Inventors: SangHoon Hur, Seoul (KR); Byungdoo Min, Seoul (KR); Jeffrey Lee, Seoul (KR)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 313 days.

(21) Appl. No.: 16/079,819

(22) PCT Filed: Feb. 24, 2017

(86) PCT No.: PCT/US2017/019309
§ 371 (c)(1),
(2) Date: Aug. 24, 2018

(87) PCT Pub. No.: WO2017/147389
PCT Pub. Date: Aug. 31, 2017

(65) Prior Publication Data
US 2020/0124583 A1    Apr. 23, 2020

Related U.S. Application Data

(60) Provisional application No. 62/300,427, filed on Feb. 26, 2016.

(51) Int. Cl.
*G01N 33/22* (2006.01)
*G01N 33/00* (2006.01)
(Continued)

(52) U.S. Cl.
CPC ....... *G01N 33/225* (2013.01); *G01N 33/0073* (2013.01); *G01N 33/227* (2013.01);
(Continued)

(58) Field of Classification Search
CPC ............ G01N 33/225; G01N 33/0073; G01N 33/227; G01N 2021/1704; G01N 21/1702;
(Continued)

(56) References Cited

U.S. PATENT DOCUMENTS 4,850,669 A * 7/1989 Welker ................. G02B 6/0005
385/75
7,714,732 B2 5/2010 Cox et al.
(Continued)

FOREIGN PATENT DOCUMENTS

| CA | 2687514 A1 | 12/2008 |
| CN | 204705586 U | 10/2015 |

(Continued)

OTHER PUBLICATIONS

International Application No. PCT/US2017/019309, International Search Report, dated Jun. 7, 2017, 6 pages.
(Continued)

*Primary Examiner* — Nimeshkumar D Patel
*Assistant Examiner* — Gedeon M Kidanu
(74) *Attorney, Agent, or Firm* — Alston & Bird LLP

(57) ABSTRACT

An explosion-proof electronic system. The system comprises a substantially explosion-proof enclosure, a disk that is free to rotate about an axis, where the disk is located within the enclosure, an optical sensor that is configured to sense rotation of the disk, where the optical sensor is located within the enclosure, and a processor that is coupled to the optical sensor and analyzes a rotation input from the optical sensor to control in part the operation of the electronic system.

20 Claims, 2 Drawing Sheets

(51) Int. Cl.
*G08B 7/06* (2006.01)
*G08B 17/117* (2006.01)
*G08B 21/18* (2006.01)

(52) U.S. Cl.
CPC .............. *G08B 7/06* (2013.01); *G08B 17/117* (2013.01); *G08B 21/182* (2013.01)

(58) Field of Classification Search
CPC .............. G01N 21/3504; G01N 21/39; G01N 2021/151; G01N 2021/1793; G01N 2021/399; G01N 21/031; G01N 21/09; G01N 21/31; G01N 21/59; G01N 21/643; G01N 21/783; G01N 2201/022; G01N 2201/0236; G01N 2201/0638; G01N 2201/0696; G01N 2201/127; G01N 2291/0427; G01N 29/2425; G01N 33/0006; G01N 33/0013; G01N 33/0027; G01N 33/0037; G01N 33/0042; G01N 33/0044; G08B 7/06; G08B 17/117; G08B 21/182; G08B 29/22; G01F 15/063; G02B 23/2476; G02B 6/0005; G02B 6/403; G02B 6/4298; G05G 2009/04744; G05G 2009/04755; G05G 2009/04762; G08C 17/04; H01F 7/0226; H01F 7/064

See application file for complete search history.

(56) References Cited

U.S. PATENT DOCUMENTS

| | | | |
|---|---|---|---|
| 8,314,711 | B2 | 11/2012 | Cox et al. |
| 8,334,787 | B2* | 12/2012 | Bushman .............. G01D 4/008 340/870.02 |
| 2006/0044562 | A1* | 3/2006 | Hagene ................. G01N 21/39 356/437 |
| 2006/0093523 | A1 | 5/2006 | Norman |
| 2006/0227113 | A1 | 10/2006 | Joyce et al. |
| 2007/0230717 | A1 | 10/2007 | Akino |
| 2009/0288474 | A1* | 11/2009 | Kalkman ............. A61B 5/0095 73/24.02 |
| 2010/0177062 | A1* | 7/2010 | Liu ....................... G06F 3/0421 345/175 |
| 2010/0283991 | A1* | 11/2010 | Chrzan .................. G01N 21/09 356/51 |
| 2014/0184367 | A1* | 7/2014 | Liao ...................... H03K 17/97 335/205 |
| 2015/0077203 | A1* | 3/2015 | Henderson ............. H01H 36/00 335/207 |
| 2016/0091418 | A1* | 3/2016 | Schachinger ...... G01N 33/0027 356/437 |
| 2016/0320361 | A1* | 11/2016 | Johansen ........... G01N 21/1702 |
| 2017/0094444 | A1* | 3/2017 | Manahan ............... G08C 17/04 |
| 2019/0304649 | A1* | 10/2019 | Freer ....................... H05K 5/03 |

FOREIGN PATENT DOCUMENTS

| | | |
|---|---|---|
| EP | 3405935 B1 | 10/2019 |
| JP | 2005338361 A | 12/2005 |
| JP | 4345310 B2 | 10/2009 |
| WO | 2017147389 A1 | 8/2017 |

OTHER PUBLICATIONS

International Application No. PCT/US2017/019309, Written Opinion of the International Searching Authority, dated Jun. 7, 2017, 7 pages.
Yokogawa Electric Corporation, User's Manual, Model ZR202S Integrated type Explosion-proof Zirconia Oxygen Analyzer, 4th Edition, Aug. 2015, pp. 1-78.
Yokogawa Electric Corporation, User's Manual, Model ZR202S Integrated type Explosion-proof Zirconia Oxygen Analyzer, 4th Edition, Aug. 2015, pp. 79-156.
International Application No. PCT/US2017/019309, International Preliminary Report on Patentability, dated Aug. 28, 2018, 8 pages.
Europe Patent Application No. 17714043.1, Communication pursuant to Rules 161(1) and 162 EPC, dated Sep. 13, 2018, 3 pages.
Decision to grant a European patent dated Sep. 19, 2019 for EP Application No. 17714043.
Intention to grant dated Jun. 4, 2019 for EP Application No. 17714043.

* cited by examiner

OPTICAL SWITCH WITH REFLECTION DISK IN EXPLOSION-PROOF GAS DETECTOR

CROSS-REFERENCE TO RELATED APPLICATIONS

The present application is the National Stage of International Application No. PCT/US2017/019309 filed Feb. 24, 2017 and entitled "Optical Switch With Reflection Disk In Explosion-Proof Gas Detector," which claims priority to U.S. Provisional Patent Application No. 62/300,427 filed Feb. 26, 2016, and entitled "Optical Switch With Reflection Disk In Explosion-Proof Gas Detector," such that the present application claims priority to both listed related applications, both of which are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Explosion-proof instruments may be employed in industrial processes or environments where explosions are a hazard, for example in industrial burners or in combustible gas distribution systems. The term "explosion-proof" may mean invulnerable to explosions below a pre-defined intensity level. Said in other words, an explosion-proof device or instrument may fail when subjected to an explosion that exceeds a defined explosion resistance capacity of the device or instrument.

SUMMARY

In an embodiment, an explosion-proof electronic system is disclosed. The explosion-proof electronic system comprises a substantially explosion-proof enclosure, a disk that is free to rotate about an axis, where the disk is located within the enclosure, an optical sensor that is configured to sense rotation of the disk, where the optical sensor is located within the enclosure, and a processor that is coupled to the optical sensor and analyzes a rotation input from the optical sensor to control in part the operation of the electronic system.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

This disclosure teaches an explosion-proof electronic device that is controllable through interaction between a magnet external to the device and a rotating optical disk located inside the device. The optical disk is free to rotate around an axis. A magnetically responsive component coupled to the disk can be moved remotely (e.g., from outside of the device) by an external magnet. For example, the component on the disk may be an iron or steel slug that is attracted to a magnet. By bringing the external magnet close to the device and moving the external magnet in a rotating motion, the iron or steel slug will be attracted by the magnet and cause the disk to rotate. An optical sensor within the device senses the rotation of the disk and provides a sensor input to a logical processor inside the device. The logical processor can control the device, at least in part, based on the sensor input, hence based on the movement of the external magnet. The magnetically responsive component coupled to the disk may be a magnet. The interaction with the external magnet may be either that of attraction or repulsion. In an embodiment, the electronic device may be an explosion-proof gas detector, and the optical disk may be controlled by an external magnet to set alarm thresholds of the gas detector, for example gas concentration alarm thresholds.

Figure 1:
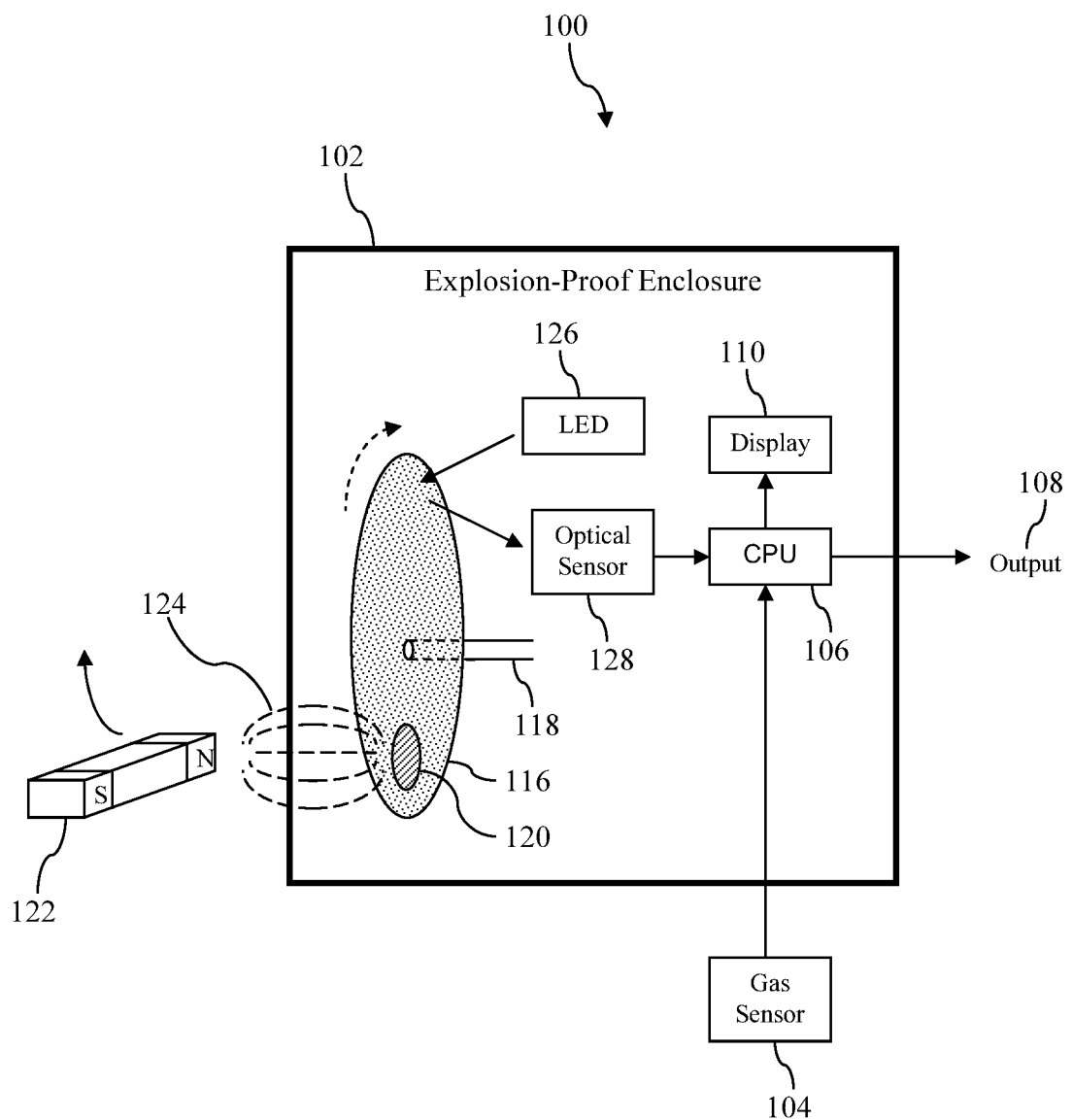
FIG. 1 is an illustration of an explosion-proof gas detector according to an embodiment of the disclosure.

Turning now to FIG. 1, an explosion-proof electronic system 100 is described. In an embodiment, the system 100 comprises an explosion-proof enclosure 102, a gas sensor 104, a processor 106, and a display 110. The system 100 further comprises an optical disk 116 mechanically coupled to an axle 118 and having a slug 120 coupled to the disk 116. The slug 120 may interact with an external magnet 122 via a magnetic field 124. The system 100 further comprises a light emitting component 126 and a light sensing component 128. It is understood that in some embodiments one or more components listed above may not be present (e.g., the display 110 may not be present) or one or more components identified as separate may be combined. In an embodiment, the explosion-proof enclosure 102 further comprises explosion-proof glass, where a plane of the optical disk 116 is substantially parallel to a plane of the glass.

It is understood that the use of the term "explosion-proof" herein does not mean that the system 100 and/or enclosure 102 cannot be damaged or destroyed by an explosion, for example an explosion whose intensity is very great. The term "explosion-proof" means substantially invulnerable to an explosion of an intensity below a pre-defined limit of intensity or below an explosion rating. This caveat may be indicated herein by the expression "substantially explosion-proof."

The processor 106 is an electronic and/or semiconductor device that is able to perform logical instructions or programs to control the system 100. As part of its function, the processor 106 may produce an output 108 that is transmitted out of the system 100, for example communicated via a communication channel to an external system and/or transmitted to a presentation device outside of the explosion-proof enclosure 102 such as to an aural alarm and/or visual alarm. The processor 106 may analyze an input from the gas sensor 104 to determine a concentration of one or more kinds of gases in an environment proximate to the system 100. If the processor 106 determines that the concentration of a gas exceeds a predefined threshold concentration, it may output an alarm on output 108.

The processor may be any of a microcontroller (MCU), a microprocessor (MPU), a central processing unit (CPU), a digital signal processor (DSP), a complex programmable logic device (CPLD), a field programmable gate array (FPGA), or an application specific integrated circuit (ASIC). In an embodiment, the processor 106 may comprise two or more separate processors, for example two of the same type of processors listed above or for example processors from different processor categories or types.

The gas sensor 104 may detect a concentration of a specific gas, for example a concentration of a combustible gas. The sensor 104 may detect a concentration of hydrocarbons in a gas state. The gas sensor 104 is depicted as being located outside of the explosion-proof enclosure 102, but in an embodiment, part of the gas sensor 104 may be located within the enclosure 102 and a different part of the gas sensor 104 may be located outside of the enclosure 102, for example a sensor probe portion of the gas sensor 104 may be located outside of the enclosure 102. In an embodiment, the system 100 may comprise a plurality of gas sensors 104. The multiple gas sensors 104 may be configured to detect different kinds of gases. Alternatively or in addition, the multiple gas sensors 104 may be redundant so that if one sensor 104 fails another sensor 104 may be relied upon in its place.

In an embodiment, the system 100 may receive electrical power from a source external to the explosion-proof enclosure 102. Alternatively, the system 100 may receive electrical power from a battery located within the explosion-proof enclosure 102.

The optical disk 116 is free to rotate on the axis of the axle 118. The optical disk 116 may be coupled to the axle 118 by bearings, for example pin-shaped bearings, that reduce rotating friction of the optical disk 116. The light emitting component 126 radiates light onto a planar face of the optical disk 116, and the light sensing component 128 senses the light reflecting off of the optical disk 116 (e.g., the light initially radiated by the light emitting component 126). The light emitting component 126 and the light sensing component 128 may be physically positioned relative to each other to promote the emitted light reflecting off the optical disk 116 to the sensor. In an embodiment, the light emitting component 126 emits infrared light. In an embodiment, the light emitting component 126 is a light emitting diode (LED), for example an infrared LED. In an embodiment, the light emitting component 126 and the light sensing component 128 may be encapsulated in a single electro-mechanical component. The planar surface of the optical disk 116 that is exposed to the light emitted by the light emitting component 126 may be manufactured to have contrasting texture or graphical patterns that enhance the function of detecting rotation of the optical disk 116 by the light sensing component 128 and/or by the processor 106 analyzing the output of the light sensing component. In an embodiment, the light sensing component 128 may be a digital camera-type of device (e.g., a charge coupled device (CCD) or other digital imaging component) that captures digital images of the surface of the optical disk 116 that is in view of the light sensing component 128 and provides these images to the processor 106. The processor 106 may analyze a time sequence of these digital images to detect rotation of the optical disk 116. The processor 106 can analyze the output of the light sensing component 128 to determine a rate of rotation (i.e., an angular velocity) and/or a directional sense (e.g., clockwise or counter clockwise) of the optical disk 116.

The slug 120 may be composed of a metal that is attracted or repulsed by a magnet. Alternatively, the slug 120 may itself be a magnet that is attracted or repulsed by a second magnet. When the external magnet 122 is brought close to the slug 120, the interaction 124 between the external magnet 122 and the slug 120 either attracts or repels the slug 120. The force on the slug 120 causes the optical disk 116 to rotate. Therefore, the external magnet 122 can be used by a human being or robotic system to provide a control input to the system 100, for example to the processor 106. The slug 120 may be coupled to the optical disk 116 by adhesive or glue. The slug 120 may be coupled to the optical disk 116 by screws, rivets, bolts, brackets, pins, clips, or other retaining hardware.

The rotation of the optical disk 116 may be controlled by the external magnet 122 to define and/or configure alarm thresholds of the system 100. The display 110 may provide visual feedback to an operator using the external magnet 122 to set alarm thresholds and/or a gas concentration threshold parameter. The system 100 may enter and exit input modes based on the rotation of the optical disk 116 and/or based on passage of time. For example, the system may be caused to enter a control input mode in response to detecting a certain number of rotations of the optical disk 116. Upon entering the control input mode, the display 110 may indicate the control input mode. The display may then indicate a parameter to be changed. If rotation of the optical disk 116 is detected, the parameter is adjusted up or down accordingly. When the rotation of the optical disk 116 stops, the parameter value is stored. If no rotation is detected over a predefined period of time (e.g., 10 seconds), the display may indicate a different parameter to be changed. By selectively rotating the optical disk 116 or not rotating the optical disk 116—by use of the external magnet 122—an operator can both step through a number of different parameters and set selected parameter values. After stepping through all the parameters, the system 100 may automatically return to an operational mode (meaning, not accepting control inputs via the optical disk 116).

The use of the optical disk 116 controlled by the external magnet 122 may provide benefits relative to known systems that may be slow to transition and respond to control inputs. It is understood that while the system 100 was described in the context of a gas sensor or gas detector, the teachings of the present disclosure are contemplated to be advantageously applicable in a variety of other systems.

Figure 2:
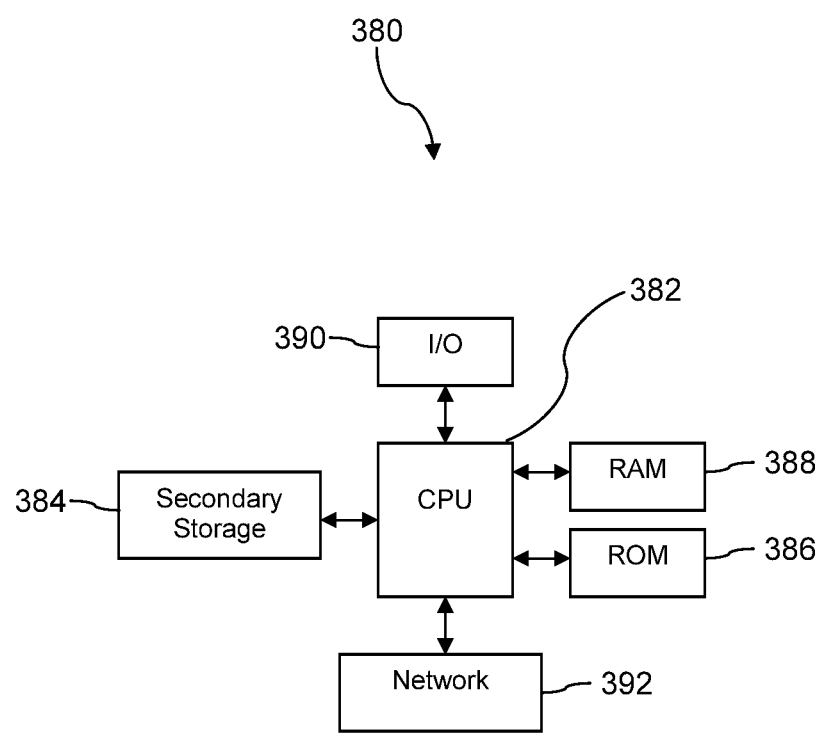
FIG. 2 is an illustration of a computer system according to an embodiment of the disclosure.

FIG. 2 illustrates a computer system 380 suitable for implementing one or more aspects of embodiments of explosion-proof electronic devices or instruments disclosed herein. It is understood that some elements of the computer system 380 illustrated in FIG. 2 and described below may not be present in some of the explosion-proof electronic systems 100, for example, in an embodiment the explosion-proof system 100 may not comprise secondary storage or network connectivity. Notwithstanding, these features are illustrated and described at least for the sake of completeness.

The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC as a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), world-wide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from a hard disk, floppy disk, optical disk (these various disk-based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other devices, the ROM 386 and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, a magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An explosion-proof electronic system, comprising:
a substantially explosion-proof enclosure;
a disk that is free to rotate about an axis, wherein the disk is located within the substantially explosion-proof enclosure, wherein the disk comprises a magnetically responsive component configured to be rotated remotely by interaction with an external magnet;
an optical sensor that is configured to sense rotation of the disk, where the optical sensor is located within the substantially explosion-proof enclosure; and
a processor that is coupled to the optical sensor and analyzes a rotation input from the optical sensor to control in part an operation of the explosion-proof electronic system.

2. The explosion-proof electronic system of claim 1, wherein the processor is one of a (MCU), a microprocessor (MPU), a central processing unit (CPU), a digital signal processor (DSP), a complex programmable logic device (CPLD), a field programmable gate array (FPGA), or an application specific integrated circuit (ASIC).

3. The explosion-proof electronic system of claim 1, wherein the magnetically responsive component comprises a steel or iron slug coupled to the disk, where the steel or iron slug is susceptible of being attracted to the external magnet.

4. The explosion-proof electronic system of claim 1, wherein the magnetically responsive component comprises a magnet coupled to the disk, the magnet is susceptible of being attracted to the external magnet.

5. The explosion-proof electronic system of claim 1, wherein the magnetically responsive component comprises a magnet coupled to the disk, where the magnet is susceptible of being repelled by the external magnet.

6. The explosion-proof electronic system of claim 1, further comprising a display coupled to the processor, where the display provides an indication of the control provided by the processor based on analysis of the rotation input from the optical sensor.

7. The explosion-proof electronic system of claim 1, further comprising substantially explosion-proof glass, where a plane of the disk is substantially parallel to a plane of the substantially explosion-proof glass.

8. The explosion-proof electronic system of claim 1, further comprising a gas sensor coupled to the processor, the processor analyzes a gas presence input from the gas sensor.

9. The explosion-proof electronic system of claim 8, wherein the gas sensor detects a concentration of a combustible gas.

10. The explosion-proof electronic system of claim 8, wherein the gas sensor detects a concentration of hydrocarbons in a gas state.

11. The explosion-proof electronic system of claim 1, the processor is configured to output an alarm when it determines presence of gas above a threshold concentration.

12. The explosion-proof electronic system of claim 11, wherein the rotation input from the optical sensor controls a concentration threshold parameter of the processor, and the processor is configured to output the alarm when it determines presence of gas above the concentration threshold parameter.

13. The explosion-proof electronic system of claim 11, wherein the alarm is an aural alarm, a visual alarm, or both.

14. The explosion-proof electronic system of claim 1, comprises a light emitting component and a light sensing component.

15. The explosion-proof electronic system of claim 14, wherein the light emitting component emits infrared light.

16. The explosion-proof electronic system of claim 14, wherein the light emitting component is positioned to radiate light onto a planar surface of the disk and the light sensing component is positioned to detect light reflected by the planar surface of the disk emitted by the light emitting component.

17. The explosion-proof electronic system of claim 16, wherein the planar surface of the disk has a contrasting texture.

18. The explosion-proof electronic system of claim 16, wherein the planar surface of the disk has graphical patterns that enhance a function of detecting rotation of the disk.

19. A system comprising:
a substantially explosion-proof enclosure;
a disk disposed within the substantially explosion-proof enclosure, wherein the disk is free to rotate about an axis, the disk comprising a magnetically responsive component configured to be rotated remotely by interaction with one or more magnets outside the substantially explosion-proof enclosure; and
an optical sensor disposed within the substantially explosion-proof enclosure, the optical sensor being configured to sense rotation of the disk and communicate information indicative of the rotation of the disk to one or more processors that are configured to analyze a rotation data corresponding to the rotation and control in part an operation of the system based on the analysis.

20. A method comprising:
providing an electronic system comprising a substantially explosion-proof container having a disk and an optical sensor disposed therein, the disk being free to rotate about an axis, the optical sensor configured to sense rotation of the disk and communicate information indicative of the rotation of the disk to one or more processors;
disposing a magnet located outside the substantially explosion-proof container and within a predetermined distance of the disk, wherein the disk is configured to rotate about the axis in response to one or more magnetic fields generated by the magnet;
sensing, using the optical sensor, rotation of the disk in response to the one or more magnetic fields generated by the magnet;
communicating information indicative of the rotation of the disk to the one or more processors; and
controlling one or more operations of the electronic system based at least upon analysis, conducted by the one or more processors, of the information indicative of the rotation of the disk.

* * * * *